United States Patent [19]

Suzuki et al.

[11] Patent Number: 4,711,776
[45] Date of Patent: Dec. 8, 1987

[54] HAIR COSMETIC COMPOSITION

[75] Inventors: Toshio Suzuki, Ichikawa; Kazuyuki Yahagi, Tokyo, both of Japan

[73] Assignee: Kao Corporation, Tokyo, Japan

[21] Appl. No.: 792,198

[22] Filed: Oct. 28, 1985

[30] Foreign Application Priority Data

Nov. 6, 1984 [JP] Japan ................ 59-233761

[51] Int. Cl.$^4$ ................ A61K 7/06; A61K 7/08; A61K 9/12
[52] U.S. Cl. ................ 424/70; 424/DIG. 1; 424/47; 514/880
[58] Field of Search ................ 424/70

[56] References Cited

FOREIGN PATENT DOCUMENTS

| | | | |
|---|---|---|---|
| 2938383 | 4/1980 | Fed. Rep. of Germany | 424/70 |
| 4619639 | 6/1971 | Japan | 424/70 |
| 0169614 | 12/1981 | Japan | 424/70 |
| 0169615 | 12/1981 | Japan | 424/70 |
| 0169616 | 12/1981 | Japan | 424/70 |
| 0050909 | 3/1982 | Japan | 424/70 |
| 0056414 | 4/1982 | Japan | 424/70 |
| 0200308 | 12/1982 | Japan | 424/70 |

*Primary Examiner*—Dale R. Ore
*Attorney, Agent, or Firm*—Oblon, Fisher, Spivak, McClelland & Maier

[57] ABSTRACT

A hair cosmetic composition contains (A) 0.01–20 wt % of one or more of specific branched quaternary ammonium salts and (B) 0.1–30 wt % of oils and fats. The hair cosmetic composition is excellent in imparting softness, smoothness and antistaticity to the hair and even when oils and fats are contained in a large amount, does not leave oily appearance or feeling on the hair.

3 Claims, No Drawings

HAIR COSMETIC COMPOSITION

BACKGROUND OF THE INVENTION (i) Field of the Invention

This invention relates to novel hair cosmetic compositions, and more specifically to hair cosmetic compositions, such as hair rinse compositions, hair conditioners, hair treatment compositions, hair creams, styling lotions, styling mousses, conditioning mooses, hair spray compositions or the like, comprising branched type alkyl quaternary ammonium salts and imparting little oily appearance and feeling, smoothness, softness and antistaticity to the hair.

(ii) Description of the Prior Art

Hair cosmetic compositions containing, as principal effective components, di(linear long-chain alkyl) quaternary ammonium salts in which the two long-chain alkyl groups are linear, such as distearyldimethylammonium chloride have heretofore been used.

Of these, hair rinse compositions are intended to impart softness, smoothness, antistaticity and the like to the hair. Sole use of a di(linear long-chain alkyl) quaternary ammonium salt cannot achieve sufficient effects in softness and smoothness. With a view toward improving these drawbacks, it has conventionally been a routine practice to incorporate oils and fats such as higher alcohol, glyceride or liquid paraffin.

Mono- or di(linear long-chain alkyl) quaternary ammonium salts have also been employed in hair creams, styling compositions and the like, in each of which oils and fats or resin is contained as its principal component, so as to impart softness, smoothness, antistaticity and the like.

By the way, di(linear straight-chain alkyl) quaternary ammonium salts do not have any ability to stably emulsify or disperse oils and fats in an amount sufficient to exhibit its effects. It has thus been attempted to incorporate a mono(linear long-chain alkyl) quaternary ammonium salt or non-ionic surface active agent having high hydrophilicity for obtaining a stable emulsion or dispersion system from an emulsion system such as cream rinse composition or the like. However, these compounds having high hydrophilicity reduce the performances of hair rinse significantly. The prior art compositions are hence accompanied by a drawback that the inherent effects of hair rinse of quaternary ammonium salts, oils and fats, cannot be fully exhibited.

Furthermore, conventional hair cosmetic compositions containing oils and fats or resins as their principal components were accompanied by a problem that conventional mono- or di(linear long-chain alkyl) quaternary ammonium salts were not able to exhibit their effects fully upon imparting softness, smoothness, antistaticity, etc.

It has thus been desired to develop a hair cosmetic composition which is excellent in imparting softness, smoothness and antistaticity even when oils and fats are present in a large amount and which does not leave oily appearance or feeling.

SUMMARY OF THE INVENTION

Under the above circumstance, the present inventors carried out an extensive research. As a result, it has been found that the above drawbacks can be overcome and excellent hair cosmetic compositions can be obtained by replacing the conventional linear long-chain alkyl quaternary ammonium salts in parts or in their entirety with specific branched quaternary ammonium salts, leading to completion of this invention.

Namely, the present invention provides a hair cosmetic composition which comprises:

(A) 0.01–20 wt.% of one or more of branched quaternary ammonium salts represented by the following formula (i) or (ii):

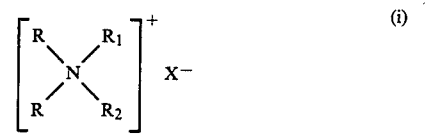

wherein R is an alkyl group selected from (a) branched alkyl groups represented by

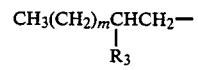

and (b) linear alkyl groups represented by $CH_3\text{-}(CH_2)_n\text{-}$, $R_3$ being a methyl or ethyl group and m and n being numbers making their corresponding alkyl groups have total carbon numbers of 8–16, the degree of branching of the group R, $(a)/\{(a)+(b)\}$ is 10–100 wt.%, $R_1$ and $R_2$ denote individually a group selected from benzyl group and alkyl or hydroxyalkyl groups having 1–3 carbon atoms, and $X^-$ means a halogen ion or organic anion,

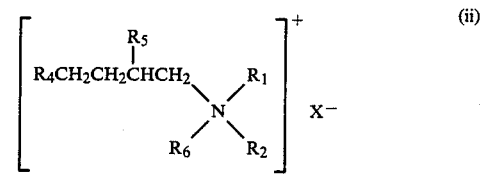

wherein $R_4$ and $R_5$ are individually an alkyl group having 2–12 carbon atoms, $R_6$ means a group

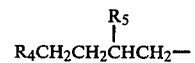

or an alkyl group having 1–3 carbon atoms, and $R_1$, $R_2$ and $X^-$ have the same meanings as defined above; and (B) 0.1–30 wt.% of oils and fats.

DETAILED DESCRIPTION OF THE INVENTION AND PREFERRED EMBODIMENTS

In the component (A) of this invention, the branched quaternary ammonium salt (i) is usually synthesized using an oxo alcohol having 8–16 carbon atoms. As its examples, may be mentioned dialkyldimethylammonium salts, dialkylmethylhydroxylethylammonium salts, dialkylmethylbenzylammonium salts and the like which contain alkyl groups derived from such alcohols. As exemplary matching ions for these ammonium salts, may be mentioned halogen ions such as chlorine, iodine and bromine ions and organic anions such as methosulfate, ethosulfate, methophosphate and ethophosphate.

In the formula (I), the alkyl group R is a group selected from (a)

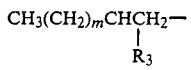

and (b) $\overline{CH_3(CH_2)_n}$, and $R_3$ is a methyl or ethyl group. The degree of branching of the group R, (a)/{(a)+(b)} is determined from the degree of branching of an oxo alcohol employed as a raw material. It may be 10-100 wt.% generally, and more preferably 10-50 wt.%. On the other hand, the total carbon number of the alkyl group R may be 8-16. It is however preferable for the alkyl group R to have a particular distribution. An alkyl group having the following distribution is particularly preferred.

| | |
|---|---|
| $C_{8-11}$: | 5 wt. % or less |
| $C_{12}$: | 10-35 wt. % |
| $C_{13}$: | 15-40 wt. % |
| $C_{14}$: | 20-45 wt. % |
| $C_{15}$: | 5-30 wt. % |
| $C_{16}$: | 5 wt. % or less |

As a particularly preferred specific example, may be mentioned a dialkyldimethylammonium chloride represented by the general formula (I) and having an alkyl group R having 8-16 carbon atoms and a degree of branching of 10-50 wt.%. When used as a hair rinse composition, this compound can impart good smoothness (slipping properties) to the hair especially when the hair is wet.

In the component (A) of this invention, the branched quaternary ammonium salt (ii) is represented by the formula (II) and is usually synthesized using a Guerbet alcohol

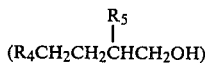

as a raw material. As preferred examples of this branched quaternary ammonium salt, may be mentioned monoalkyl quaternary ammonium salts such as alkyltrimethylammonium salts, alkyldimethylhydroxyethylammonium salts and alkyldimethylbenzylammonium salts; dialkyldimethylammonium salts; dialkylmethylhydroxyethylammonium salts; dialkylmethylbenzylammonium salts; and the like. They all contain alkyl groups derived from Geurbet alcohols. Illustrative of matching ions to these ammonium salts include halogen ions such as chlorine, iodine and bromine ions and organic anions such as methosulfate, ethosulfate, methophosphate and ethophosphate. As exemplary alkyl groups derived from Guerbet alcohols, may be mentioned 2-hexyldecyl, 2-octyldodecyl, 2-decyltetradecyl and 2-dodecyhexadecyl groups. As particularly preferred specific examples of the branched quaternary ammonium salt (II), there are 2-decyltetradecyltrimethylammonium chloride, 2-dodecylhexadecyltrimethylammonium chloride, di-2-hexyldecyldimethylammonium chloride, di-2-octyldodecylammonium chloride, etc. When used as hair rinse compositions, these compounds can impart good smoothness (slipping properties) to the hair particularly when the hair is dry.

These quaternary ammonium salts represented by the formula (I) or (II) may be used either singly or in combination. They may be incorporated in a hair cosmetic composition in a total amount of 0.01-20 wt.% or preferably 0.05-5 wt.%.

In the cosmetic composition of this invention, it is also possible to use as auxiliary component or components quaternary ammonium salts other than those described above, for example, cetylmethylammonium chloride, stearyltrimethylammonium chloride and/or the like.

As the oils or fats which are incorporated as the component (B), it is feasible to use any one of those employed routinely. Liquid paraffin, glycerides, higher alcohols, lanolin derivatives, esters, higher fatty acids and the like may be mentioned by way of example. Of these oils and fats, monoglycerides derived from saturated or unsaturated, linear of branched fatty acids having 12-24 carbon atoms and higher alcohols containing linear or branched alkyl or alkenyl groups having 12-26 carbon atoms are particularly preferred for hair rinse compositions or hair conditioners. As their preferred specific examples, may be mentioned fatty acid monoglycerides such as oleic monoglyceride, palmitic monoglyceride, stearic monoglyceride, behenic monoglyceride and isostearic monoglyceride and higher alcohols such as cetyl alcohol, stearyl alcohol, arachidyl alcohol, behenyl alcohol, caranabyl alcohol and ceryl alcohol.

In the hair cosmetic composition of this invention, this component (B) may be incorporated in an amount of 0.1-30% or preferably 0.3-10%.

The hair cosmetic composition of this invention may be prepared in a manner known per se in the art, for example, by adding the above components (A) and (B) to heated water and then cooling the resultant aqueous mixture with stirring. Upon preparation of the hair cosmetic composition, a solvent such as alcohol, propylene glycol or glycerin may also be used. In this case, it is preferable to adjust the pH of the solvent with an organic acid such as citric acid or lactic acid, inorganic acid such as phosphoric acid or hydrochloric acid, inorganic alkaline material such as caustic soda, organic alkaline material such as triethanolamine or the like as needed, whereby its 5% aqueous solution has a pH in the range of from 3 to 8 as usual hair rinse compositions.

It is also possible to suitably incorporate, as needed, pharmaceutically effective components such as antidandruff agents and vitamins, antiseptics such as parabens, thickeners such as water-soluble high m.w. substances, colorants such as dyes and pigments, conditioning agents such as cationic polymers, pearling agents such as glycol esters, various perfume formulations, etc. in the hair cosmetic composition of this invention.

Particularly-preferred formulation ranges of hair cosmetic compositions according to this invention, inclusive of optional components, are given in the following table.

TABLE

| | Hair rinse Hair conditioner wt % | Hair cream Hair treatment wt % | Styling lotion Styling moose Hair spray wt % |
|---|---|---|---|
| Branched quaternary ammonium salt (Component A) | 0.1-10 | 0.1-10 | 0.1-10 |
| Oils and Fats (Component B) | 0.3-10 | 2-30 | 0.3-10 |
| Surface active agent except Component A | 0-5 | 2-10 | 0-5 |
| Synthetic resins | 0-1 | 0-5 | 0-5 |
| Water | 60-99.5 | 40-95 | 60-99.5 |

TABLE-continued

| | Hair rinse Hair conditioner wt % | Hair cream Hair treatment wt % | Styling lotion Styling moose Hair spray wt % |
|---|---|---|---|
| Other components | 0-20 | 0-20 | 0-20 |

For aerosols such as mousses and hair sprays, propellants such as fluorocarbon, liquefied petroleum gas and dimethyl ether are used in addition to the above-described components to build up internal pressures of 2.0–6.0 kg/cm²G, in other words, in amounts of 1–20 wt.% based on the whole compositions.

Hair cosmetic compositions according to this invention have little oily appearance and feeling, are particularly effective in imparting smoothness, softness and antistaticity to the hair, and enjoy good stability.

The present invention will next be described by the following Examples. It should however be borne in mind that the present invention is not limited to or by the following Examples. The following testing methods were employed in the Examples.

(1) Appearance:
A sample was placed in a 100 ml transparent glass container and its appearance was visually observed. Its evaluation results are indicated on the basis of the following standard:
○ : thoroughly homogeneous; problems such as separation and/or coagulation were not observed.
X: heterogeneous; separation and/or coagulation was observed.

(2) Organoleptic evaluation:
Twenty grams of the hair (length: 15 cm) of a Japanese lady which has not received any beauty treatment such as cold wave or bleach was bundled. Two grams of a hair rinse composition were evenly applied to the bundled hair. After washing the bundled hair for 30 seconds in running water, it was dried with a towel. The softness and oily appearance and feeling of the bundled hair in its wet state were organoleptically evaluated. In comparison with results obtained using a commercially available hair rinse composition, evaluation results are indicated on the basis of the following standard:
◎ : Far better
○ : better
Δ: comparable
X: inferior (3) Combing force:
The force required to comb (which is called "combing force" herein) a bundle of hair, which had been treated in the same manner as the organoleptic evaluation (2), was measured by a strain gauge either as was (with a water content of about 0.7 g/gram-hair) or after dried for about 5 minutes in a drier (with a water content of about 0.1 g/gram-hair). The measurement was repeated 20 times in a room air-conditioned at 20° C. and 65% R.H. Their average value (g) is employed as the combing force.

(4) Quantity of produced static electricity:
The above bundle of hair in its dry state was combed 10 times in a room air-conditioned at 20° C. and 65% R.H. The quantity of static electricity (kv) produced on the hair was measured.

(5) Friction coefficient of the surface of the hair:
A hair sample of 20 cm long and about 50 μm thick was shampooed twice, followed by a uniform application of 0.5 g of a hair rinse composition on the hair. In a room air-conditioned at 20° C. and 65% R.H., a single string of the thus-treated hair was caused to wrap a nylon pulley and weights, each of 0.5 g, were hung respectively from both ends of the hair string. Both hair string and pulley were washed with about 2 g of water. The pulley was then rotated at 5 rpm, and the difference in tension between both ends of the hair string was detected by a strain gauge. Based on a value upon an elapsed time of a predetermined period after initiation of the rotation, its dynamic friction coefficient was determined. Ten or more hair strings were measured with respect to each liquid sample and their friction coefficients were averaged.

EXAMPLE 1

Compositions shown in Tables 1 and 2 were prepared, and their appearance and performances were investigated.

Preparation of compositions:
Added to water (4) which had been heated to 70° C. were the components (1) and (3) or components (2) and (3) which had also been heated to the same temperature and thus molten. After stirring and emulsifying the resultant mixture, it was allowed to cool down to room temperature with stirring to provide a hair rinse composition. Results are given in Tables 1 and 2.

TABLE 1

| | Component | Comparative product 1 | Inventive product 1 |
|---|---|---|---|
| (1) | Dialkyldimethylammonium chloride* (%) (Component A) | — | 2.0 |
| (2) | Dicetostearyldimethylammonium chloride (%) | 2.0 | — |
| (3) | Cetyl alcohol (%) (Component B) | 3.0 | 3.0 |
| (4) | Water (%) | 95.0 | 95.0 |

| Appearance | White emulsion (Dispersed system) | Semi-transparent gel (Liquid crystal system) |
|---|---|---|

Effects on hair:

| | | | |
|---|---|---|---|
| (1) | Combing force (g) | | |
| | wet state | 226 | 195 |
| | dry state | 139 | 70 |
| (2) | Organoleptic evaluation | | |
| | non-oiliness | X | ◎ |
| | softness | Δ | ◎ |
| (3) | Quantity of produced | 1.8 | 1.4 |

TABLE 1-continued static electricity (kv)

*Branched quarternary ammonium (degree of branching = 20 wt %) which is derived from commercially available oxo synthesized alcohol having from 12 to 15 carbon atoms (equivalent mixture of DOVANOL 23 and DOVANOL 45, product of Mitsubishi Petrochemical Co., Ltd.)

TABLE 2

| Component | Comparative product 2 | Inventive product 2 | Inventive product 3 | Inventive product 4 | Inventive product 5 |
|---|---|---|---|---|---|
| (1) Dialkyldimethyl-ammmonium chloride* (%) (Component A) | — | 2.0 | 2.0 | 2.0 | 2.0 |
| Degree of branching of dialkyldimethyl ammonium chloride (%) | — | 21.2 | 39.4 | 57.6 | 94.0 |
| (2) Dilauryldimethyl-ammonium chloride (%) | 2.0 | — | — | — | — |
| (3) Cetyl alcohol (%) (Component B) | 3.0 | 3.0 | 3.0 | 3.0 | 3.0 |
| (4) Water (%) | 95.0 | 95.0 | 95.0 | 95.0 | 95.0 |
| Appearance | ◯ | ◯ | ◯ | ◯ | ◯ |
| Effects on hair: | | | | | |
| (1) Dynamic friction coefficient in wet state | 0.130 | 0.120 | 0.116 | 0.137 | 0.145 |
| (2) Organoleptic evaluation | | | | | |
| non-oiliness | △ | ◎ | ◎ | ◎ | |
| softness | △ | ◯ | ◎ | ◎ | |
| (3) Quantity of produced static electricity (kv) | 1.48 | 1.35 | 1.05 | 0.61 | 0.34 |

*Commercially available oxo synthesized alcohol having from 12 to 13 carbon atoms (DOVANOL 23 and DOVANOL 23I, product of Mitsubishi Petrochemical Co., Ltd.)

EXAMPLE 2

The hair rinse compositions shown in Table 3 were prepared and were examined their appearance and effects on hair.

Preparation Procedure:

Into water (5) heated 70° C. were added the mixture of components (1), (3) and (4), or alternatively, (2), (3) and (4) which had also been heated to 70° C. to dissolve. After emusified by agitation, the system was cooled down to room temperature while stirring to obtain a hair rinse composition.

Results are shown in Table 3.

EXAMPLE 3

Hair rinse compositions of the following formulations were prepared. Their effects on hair were evaluated by 19 female panelists in accordance with the paired comparison method. The evaluation was made on the basis of a standard in which +2 was given to very good results and +1 was given to good results. Evaluation results are summarized in Table 4. Invention Product No. 10:

| | |
|---|---|
| (1) Dialkyldimethylammonium chloride* | 2.0% |
| (2) Cetyl alcohol | 3.0 |

TABLE 3

| Component | Inventive product 6 | Inventive product 7 | Inventive product 8 | Inventive product 9 | Comparative product 3 |
|---|---|---|---|---|---|
| Component A: | | | | | |
| (1) Dialkyldimethylammonium chloride* (%) | 0.05 | 0.5 | — | — | — |
| (2) 2-Hexyldecyltrimethyl-ammonium chloride** (%) | — | — | 0.05 | 1.0 | — |
| (3) Monostearyltrimethyl-ammonium chloride (%) | 0.5 | 0.5 | 0.15 | 0.5 | 0.5 |
| Component B: | | | | | |
| (4) Cetostearyl alcohol (%) | 2.0 | 2.0 | 2.0 | 2.0 | 2.0 |
| (5) Purified water (%) | 97.45 | 95.5 | 97.8 | 96.5 | 97.5 |
| Appearance | ◯ | ◯ | ◯ | ◯ | ◯ |
| Effects on hair: | | | | | |
| (1) Combing force (g) | | | | | |
| wet state | 195 | 188 | 196 | 180 | 240 |
| dry state | 88 | 82 | 80 | 70 | 140 |
| (2) Organoleptic test | | | | | |
| non-oiliness | ◎ | ◎ | ◯ | ◎ | △ |
| softness | ◯ | ◎ | ◎ | ◎ | △ |

*Branched quaternary ammonium salt (degree of branching = 20 wt %) which is derived from commercially available oxo synthesized alcohol having from 12 to 15 carbon atoms (equivalent mixture of DOVANOL 23 and DOVANOL 45, product of Mitsubishi Petrochemical Co., Ltd.).
**Synthesized by using Guerbet alcohol (NG ECOLE 160B, product of MITSUBISHI KASEI K. K.).

-continued

| | |
|---|---|
| (3) Propylene glycol | 5.0 |
| (4) Water | 89.6 |
| (5) Perfume | 0.4 |

*Derived from a commercial alcohol synthesized by the oxo process and having 12-15 carbon atoms [an 1:1 (by volume) mixture of DOVANOL 23 and DOVANOL 45, both products of Mitsubishi Petrochemical Co., Ltd.]. A branched quaternary ammonium salt having a degree of branching of 20%.

To the water (4) which had been heated to 70° C., were added the mixture of the components (1)-(3) which had also been heated to the same temperature and was hence in a molten state. After stirring and emulsifying the resultant mixture, the emulsion was cooled to 45° C. with stirring and after adding the perfume (5), the resultant mixture was cooled further to room temperature with stirring to obtain a hair rinse composition.

| Comparative Product No. 4: | |
|---|---|
| (1) Dicetyldimethylammonium chloride* | 2.0% |
| (2) Cetyl alcohol | 3.0 |
| (3) Propylene glycol | 5.0 |
| (4) Water | 89.6 |
| (5) Perfume | 0.4 |

To the water (4) which had been heated to 70° C., were added the mixture of the components (1)-(3) which had also been heated to the same temperature and was hence in a molten state. After stirring and emulsifying the resultant mixture, the emulsion was cooled to 45° C. with stirring and after adding the perfume (5), the resultant mixture was cooled further to room temperature with stirring to obtain a hair rinse composition.

TABLE 4

| Evaluation Remarks | Comparative product 4 | | | Inventive product 10 | |
|---|---|---|---|---|---|
| | +2 | +1 | 0 | +1 | +2 |
| 1. Total evaluation | 0 | 5 | 6 | 7 | 1 |
| 2. Finger combing when rinsing hair | 0 | 2 | 7 | 8 | 2 |
| 3. Flexibility of hair when rinsing | 0 | 2 | 8 | 8 | 1 |
| 4. Non-oiliness of hair after drying | 0 | 2 | 9 | 8 | 0 |
| 5. Smoothness of hair after drying | 0 | 1 | 9 | 7 | 2 |
| 6. Excellence in combing after drying hair | 0 | 2 | 9 | 8 | 0 |

EXAMPLE 4

To the mixture of the components (6), (7), (8) and (10) shown in Table 5 which mixture had been heated to 70° C., was added the mixture of the components (1)-(5) which had also been heated to the same temperature and was hence in a molten state. After stirring and emulsifying the resultant mixture, the emulsion was cooled to 45° C. with stirring, and after adding the perfume (9), the resultant mixture was cooled further to room temperature with stirring to obtain a hair rinse composition.

The thus-obtained hair rinse compositions all showed good rinsing performances and had good stability.

TABLE 5

| Component (%) | Inventive product 11 | → 12 | → 13 | → 14 | → 15 | → 16 | → 17 |
|---|---|---|---|---|---|---|---|
| (1) Dialkyldimethylammonium chloride* (Component A) | 4.0 | 2.0 | 1.0 | 1.0 | 0.5 | 1.0 | 0.05 |
| Dicetostearyldimethylammonium chloride | — | 1.0 | 1.0 | — | — | — | — |
| Cetostearyltrimethylammonium chloride | — | — | 1.0 | 3.0 | 1.0 | 1.0 | 1.0 |
| Behenyltrimethylammonium chloride (Component A) | 1.0 | — | — | — | — | — | — |
| (2) Cetostearyl alcohol | 4.0 | 2.0 | 3.0 | 3.0 | 2.0 | 2.0 | — |
| Behenyl alcohol | — | — | — | — | 1.0 | — | 2.0 |
| (3) Polyoxyethylene cetylether (EO = 20) | 0.2 | — | — | — | — | — | — |
| Polyoxyethylene oleylether (EO = 20) | — | 0.2 | — | 0.2 | — | — | — |
| Polyoxyethylene oleylether (EO = 5) | — | — | 0.2 | 0.2 | — | — | — |
| (4) Liquid paraffin | 1.0 | — | — | — | — | — | — |
| Stearic monoglyceride | — | 0.5 | — | — | — | — | — |
| Stearic acid | — | — | 0.5 | — | — | — | — |
| Lanoline | — | — | — | 0.5 | — | — | — |
| Myristyl myristate | — | — | — | — | — | 0.5 | — |
| (5) Propylene grycol | 3.0 | 3.0 | 3.0 | 3.0 | 3.0 | 3.0 | 3.0 |
| (6) Hydroxyethylcellulose | 0.2 | — | 0.5 | 0.5 | — | — | 0.8 |
| Hydroxymethylcellulose | — | 0.2 | — | — | — | — | — |
| (7) Anitseptic | suitable amount | → | → | → | → | → | → |
| (8) Colorant | small amount | → | → | → | → | → | → |
| (9) Perfume | small amount | → | → | → | → | → | → |
| (10) Purified water | balance 100% | → | → | → | → | → | → |

*Branched quaternary ammonium salt (degree of branching = 20 wt %) which is derived from commercially available oxo synthesized alcohol having from 12 to 15 carbon atoms (equivalent mixture of DOVANOL 23 and DOVANOL 45, product of Mitsubishi Petrochemical Co., Ltd.).

EXAMPLE 5

Hair rinse compositions were prepared in the same manner as Example 2 and were examined their efficacy.

TABLE 6

| Component | Comparative product | Inventive product 18 | → 19 | → 20 | → 21 | → 22 |
|---|---|---|---|---|---|---|
| Cetyltrimethylammonium chloride (%) | 2.0 | — | — | — | — | — |
| Component A: | | | | | | |
| 2-Hexyldodecyltrimethylammoniun chloride | — | 2.0 | — | — | — | — |
| 2-Decyltetradecyltrimethylammonium chloride | — | — | 2.0 | — | — | — |
| 2-Dodecylhexadecyltrimethylammonium chloride | 3.0 | — | — | 3.0 | — | — |
| Di-2-hexyldecyldimethyl- | — | — | — | — | 2.0 | — |

TABLE 6-continued

| Component | Comparative product | Inventive product 18 | → 19 | → 20 | → 21 | → 22 |
|---|---|---|---|---|---|---|
| ammonium chloride | | | | | | |
| Di-2-decyltetradecyldi-methylammonium chloride | — | — | — | — | — | 2.0 |
| Component B: | | | | | | |
| Cetyl alcohol | 3.0 | 3.0 | 3.0 | 3.0 | 3.0 | 3.0 |
| Water | 95.0 | 95.0 | 95.0 | 95.0 | 95.0 | 95.0 |
| Appearance | ○ | ○ | ○ | ○ | ○ | ○ |
| Effects on hair: | | | | | | |
| (1) Dynamic friction coefficient | | | | | | |
| wet state | 0.200 | 0.137 | 0.131 | 0.103 | 0.109 | 0.109 |
| dry state | 0.110 | 0.109 | 0.100 | 0.98 | 0.95 | 0.92 |
| (2) Organoleptic test | | | | | | |
| non-oiliness | △ | ◎ | ◎ | ○ | ○ | ○ |
| softness | △ | ○ | ◎ | ◎ | ◎ | ◎ |

EXAMPLE 6

Hair treatment composition:

| | | |
|---|---|---|
| (1) Dialkyldimethylammonium chloride [same as the component (1) in Ex. 1] | 1.0% |
| (2) Monostearyltrimethylammonium chloride | 1.0 |
| (3) Cetostearyl alcohol | 2.0 |
| (4) Lanolin | 3.0 |
| (5) Paraffin | 3.0 |
| (6) Polypeptide (collagen hydrolysate) | 5.0 |
| (7) Cationized cellulose | 3.0 |
| (8) Polyoxyethyleneoleyl ether (EO = 5) | 0.5 |
| (9) Methyl paraben | 0.2 |
| (10) Perfume | 0.4 |
| (11) Water | balance |
| | 100.0% |

Preparation Procedure:

The components (6), (7) and (9) were evenly dispersed in the water (11) and the resultant mixture was heated. With stirring, a homogeneous solution of the components (1), (2), (3), (4), (5) and (8) which had been heated was added, followed by cooling of the resultant mixture. Thereafter, the perfume (10) was added further to obtain a hair treatment composition which was able to impart good feeling to touch.

EXAMPLE 7

Hair cream composition:

| | |
|---|---|
| (1) Di(2-decyl)tetradecyldimethyl-ammonium chloride | 2.0 |
| (2) Cetyltrimethylammonium chloride | 1.0 |
| (3) Polyoxyethylenesorbitan monostearate (EO = 20) | 0.5 |
| (4) 2-Ethylhexanoic triglyceride | 2.5 |
| (5) Dipropylene glycol | 6.0 |
| (6) Glycerin | 10.0 |
| (7) Liquid paraffin | 3.0 |
| (8) Cetanol | 1.5 |
| (9) Perfume | 0.4 |
| (10) Water | balance |
| | 100.0% |

Preparation Procedure:

To the water (10) which had been heated, was added a homogeneous solution of the components (1), (2), (3), (4), (5), (6), (7) and (8) which had also been heated. After cooling of the resultant mixture, the perfume (9) was added to obtain a hair cream composition which was able to impart good feeling to touch.

EXAMPLE 8

Styling lotion composition:

| | |
|---|---|
| (1) 2-Hexyldodecyltrimethylammonium chloride | 0.5% |
| (2) Polyethylene glycol | 0.5 |
| (3) Palmitic monoglyceride | 0.5 |
| (4) Acrylic resin solution | 5.0 |
| (5) Polyethylene glycol | 1.0 |
| (6) methacrylic ester polymer | 1.0 |
| (7) Ethanol | 20.0 |
| (8) Perfume | 0.3 |
| (9) Water | balance |
| | 100.0% |

Preparation Procedure:

With stirring, the components (1), (2), (3), (4), (5), (6) and (8) were evenly dispersed in the ethanol (7). Thereafter, the perfume (9) was added to obtain a styling lotion composition which was able to impart, to the hair, good feeling to touch and excellent hair-style holding capacity.

EXAMPLE 9

Conditioning mousse composition:

| | |
|---|---|
| (1) Dialkyldimethylammonium chloride [same as the component (1) of Ex. 1] | 0.5% |
| (2) Octyldodecyl myristate | 1.0 |
| (3) Dipropylene glycol | 1.0 |
| (4) Cetanol | 1.0 |
| (5) Glycerin | 2.5 |
| (6) Liquid paraffin | 2.5 |
| (7) Polyoxyethylenesolbitan monostearate | 0.2 |
| (8) Alcohol | 5.0 |
| (9) Methyl paraben | 0.1 |
| (10) Perfume | 0.1 |
| (11) Propellant (LPG) | 10.0 |
| (12) Water | balance |
| | 100.0% |

Preparation Procedure:

The methyl paraben (9) was added to the water (12), followed by heating of the resultant mixture. With stirring, a homogeneous solution of the components (1), (2), (3), (4), (5), (6) and (7) which had been added was added further. After cooling the resultant mixture, the components (8) and (10) were incorporated further. The thus-obtained composition was filled in an aerosol can and the propellant (11) was filled therein to obtain a conditioning mousse composition capable of imparting good feeling to touch.

What is claimed is:

1. A hair cosmetic composition comprising:

(A) 0.01-20 wt. % of one or more of branched quaternary ammonium salts represented by the following formula (i) or (ii):

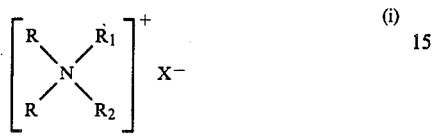

wherein R is an alkyl group selected from (a) branched alkyl groups represented by

and (b) linear alkyl groups represented by $CH_3\text{-}(CH_2)_{\overline{n}}$, $R_3$ being a methyl or ethyl group, $m=3\text{-}12$ and $n=7\text{-}15$, the degree of branching of the group R, defined as $(a)/\{(a)+(b)\}$ is 10-100 wt. %, $R_1$ and $R_2$ denote independently an organic group selected from the group consisting of a benzyl group, alkyl groups having 1-3 carbon atoms and hydroxyalkyl groups having 1-3 carbon atoms, and $X^-$ means a halogen or organic anion,

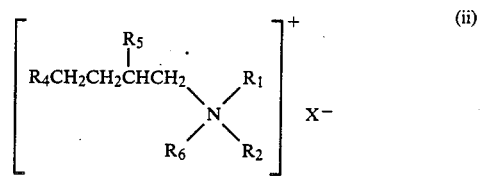

wherein $R_4$ and $R_5$ are independently an alkyl group having 2-12 carbon atoms, $R_6$ means a group

or an alkyl group having 1-3 carbon atoms, and $R_1$, $R_2$ and $X^-$ have the same meanings as defined above; and (B) 0.1-30 wt. % of oils and fats selected from the group consisting of a higher alcohol containing a linear or branched alkyl or alkenyl group having 12-26 carbon atoms and a fatty acid monoglyceride derived from saturated or unsaturated, linear or branched fatty acids having 12-24 carbon atoms.

2. A hair cosmetic composition according to claim 1 wherein the branched quaternary ammonium salts are of formula (i).

3. A hair cosmetic composition according to claim 1 wherein the branched quaternary ammonium salts are of formula (ii).

* * * * *